(12) United States Patent
Li et al.

(10) Patent No.: US 8,882,694 B2
(45) Date of Patent: Nov. 11, 2014

(54) IMPLANTABLE THREE-WAY DIAPHRAGM VALVE

(75) Inventors: Yuan-Ping Li, Duluth, GA (US); Sherri Jane Hall, Baltimore, MD (US); Kelvin Hong, Woodstock, MD (US); Shishira Nagesh, Baltimore, MD (US); Mary Katherine O'Grady, Baltimore, MD (US); Thomas Reifsnyder, Baltimore, MD (US); Thora Thorgilsdottir, Baltimore, MD (US); Clifford R. Weiss, Annapolis, MD (US); Brandon Doan, Peoria, AZ (US); Soumyadipta Acharya, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/487,590

(22) Filed: Jun. 4, 2012

(65) Prior Publication Data

US 2013/0060325 A1   Mar. 7, 2013

Related U.S. Application Data

(60) Provisional application No. 61/493,021, filed on Jun. 3, 2011.

(51) Int. Cl.
*A61M 37/00* (2006.01)
*A61M 39/22* (2006.01)
*A61F 2/06* (2013.01)

(52) U.S. Cl.
CPC ............. *A61M 39/22* (2013.01); *A61M 39/223* (2013.01); *A61F 2/06* (2013.01); *A61M 39/227* (2013.01)
USPC ......................................................... 604/6.1

(58) Field of Classification Search
CPC .............. A61M 39/22; A61M 39/223–39/227; A61M 2039/22; A61M 2039/223; A61M 2039/2433; A61M 2039/2446; A61M 2039/246; F16K 7/12–7/17; F16K 11/02–11/025
USPC ........................... 604/4.01–6.16; 251/45, 61.1
See application file for complete search history.

(56) References Cited

U.S. PATENT DOCUMENTS

| | | | |
|---|---|---|---|
| 5,931,829 A | 8/1999 | Burbank et al. | |
| 6,544,206 B1 | 4/2003 | Johnston, Jr. | |
| 6,565,525 B1 | 5/2003 | Burbank et al. | |
| 6,582,409 B1 | 6/2003 | Squitieri | |
| 6,595,941 B1 | 7/2003 | Blatter | |
| 6,663,590 B2 | 12/2003 | Blatter | |
| 6,743,218 B2 | 6/2004 | Maginot et al. | |

(Continued)

*Primary Examiner* — Philip R Wiest
*Assistant Examiner* — Benjamin Klein
(74) *Attorney, Agent, or Firm* — Johns Hopkins Technology Transfer (57) ABSTRACT

An embodiment in accordance with the present invention provides a valve including a housing having a top portion and a bottom portion. The top portion of the housing defines a first and second nozzle, and the bottom portion of the housing defines an opening. A diaphragm has an open position and a closed position, and the diaphragm is disposed between the top portion of the housing and the bottom portion of the housing. A first fluid flow path between the first nozzle and the second nozzle is defined by the housing and the diaphragm, when the diaphragm is in the closed position. A second fluid flow path between the opening and the first nozzle is defined by the housing and the diaphragm, when the diaphragm is in the open position. Such a valve can be used for a number of purposes including hemodialysis procedures.

14 Claims, 9 Drawing Sheets

(56) References Cited

U.S. PATENT DOCUMENTS

| | | |
|---|---|---|
| 7,118,546 B2 | 10/2006 | Blatter |
| 7,766,853 B2 | 8/2010 | Lane |
| 7,828,781 B2 | 11/2010 | Edoga et al. |
| 2007/0135775 A1 | 6/2007 | Edoga et al. |
| 2008/0281249 A1 | 11/2008 | Gertner |
| 2010/0019178 A1* | 1/2010 | Wilson et al. ............... 251/61.1 |
| 2011/0257577 A1* | 10/2011 | Lane et al. .................. 604/6.11 |
| 2011/0288495 A1* | 11/2011 | Claude et al. ................ 604/246 |

* cited by examiner

FIG. 5
Amended

FIG. 6
Amended

IMPLANTABLE THREE-WAY DIAPHRAGM VALVE

CROSS REFERENCE TO RELATED APPLICATIONS

This application claims the benefit of U.S. Provisional Patent Application No. 61/493,021, filed Jun. 3, 2011, which is incorporated by reference herein, in its entirety.

FIELD OF THE INVENTION

The present invention relates generally to renal therapy. More particularly, the present invention relates to a valve for facilitating hemodialysis.

BACKGROUND OF THE INVENTION

Approximately 300,000 patients undergo hemodialysis in the United States alone, with approximately 100,000 new hemodialysis patients being added each year. In order to perform hemodialysis, vascular access to the patient's blood stream is required. Currently, the options for permanent hemodialysis access are fistulas and grafts, which generally speaking are abnormal connections made between a peripheral artery and vein. Such connections essentially bypass the capillary system, thereby providing the larger flow rates required for hemodialysis. However, the life span of grafts and fistulas are low: 3 to 4 years for fistulas and 1.5 years for grafts.

Also, these connections require many interventions during their lifespan, which not only increases morbidity, but also adds large costs to the healthcare system. The failure of these connections is related to the development of stenosis due to constant large flow rates. After, repeated surgeries an access site will fail and a new access site is used until no access sites are left. A lack of remaining access sites accounts for 18% of hemodialysis patient mortality. In addition, innovation related to vascular access for hemodialysis has focused on incremental improvements to grafts and catheters, with little to no development of alternative methods and devices.

It would therefore be advantageous to provide a valve to facilitate hemodialysis that does not require the connection of an artery and vein using a graft or fistula.

SUMMARY OF THE INVENTION

The foregoing needs are met, to a great extent, by the present invention, wherein in one aspect, a valve includes a housing having a top portion and a bottom portion. The top portion of the housing defines a first nozzle and a second nozzle. The bottom portion of the housing defines an opening. The valve also includes a diaphragm having an open position, such that the diaphragm sits in a valve seat defined by the top portion of the housing. The diaphragm also has a closed position, such that the diaphragm sits in a valve seat defined by the bottom portion of the housing. The diaphragm is disposed between the top housing portion and the bottom housing portion.

In accordance with another aspect of the present invention the valve includes a first fluid flow path between the first nozzle and the second nozzle. The first fluid flow path is defined by the housing and the diaphragm, when the diaphragm is in the closed position. A second fluid flow path between the opening and the first nozzle is defined by the housing and the diaphragm, when the diaphragm is in the closed position. The diaphragm is configured to be movable from the open position to the closed position using positive pressure. The diaphragm further is movable from the closed position to the open position using negative pressure.

According to another aspect of the present invention, the housing and diaphragm are formed from biocompatible materials, and the diaphragm can be formed from an implantable grade silicone. Additionally, the diaphragm being coated with an antithrombogenic material or ePTFE. The bottom portion of the housing further includes a skirt configured to be secured to tissue. The skirt is formed from a material selected from one of the group consisting of Dacron and PTFE. The top portion of the housing has ridges along an outer surface of the top portion of the housing. A fluted opening can also be included to direct the flow of blood. The first and second nozzles can include connectors, such as barbed, press-fit, friction, twist and lock, luer, and threaded connectors.

In accordance with yet another aspect of the present invention, a valve for use in a hemodialysis device includes a housing having a top portion and a bottom portion. The top portion of the housing defines a first and second nozzle, and the bottom portion of the housing defines an opening. A diaphragm has an open position and a closed position, and the diaphragm is disposed between the top portion of the housing and the bottom portion of the housing. A first fluid flow path between the first nozzle and the second nozzle is defined by the housing and the diaphragm, when the diaphragm is in the closed position. A second fluid flow path between the opening and the first nozzle is defined by the housing and the diaphragm, when the diaphragm is in the closed position.

In accordance with still another aspect of the present invention, the bottom portion of the housing further includes a skirt configured to be secured to a large-diameter blood vessel. The top portion of the housing has ridges along an outer surface of the top portion of the housing. The valve further includes a fluted opening to direct the flow of blood. The first nozzle and the second nozzle can further include connectors, such as barbed, press-fit, friction, twist and lock, luer, and threaded connectors.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a valve including a housing having a top portion and a bottom portion. The top portion of the housing defines a first and second nozzle, and the bottom portion of the housing defines an opening. A diaphragm has an open position and a closed position, and the diaphragm is disposed between the top portion of the housing and the bottom portion of the housing. At any one time two of the first and second nozzle and opening are open and one is closed. A first fluid flow path between the first nozzle and the second nozzle is defined by the housing and the diaphragm, when the diaphragm is in the closed position. A second fluid flow path between the opening and the first nozzle is defined by the housing and the diaphragm, when the diaphragm is in the closed position. Such a valve can be used for a number of purposes including hemodialysis procedures.

Figure 1:
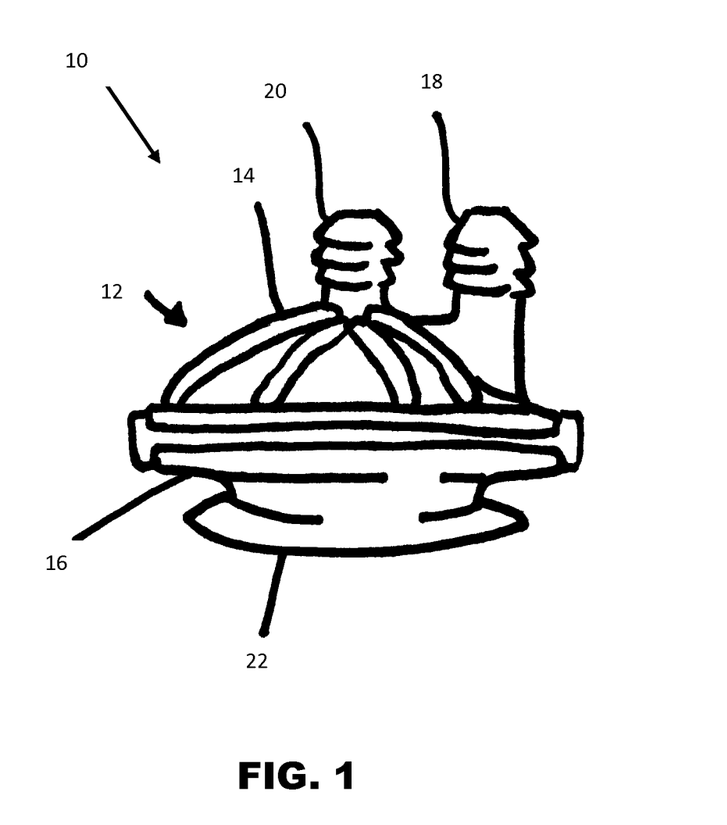
FIG. 1 illustrates a side view of a valve assembly, according to an embodiment of the invention.

FIG. 1 illustrates a side view of a valve assembly 10, according to an embodiment of the invention. As illustrated in FIG. 1, the valve assembly 10 includes a housing 12 having a top portion 14 and a bottom portion 16. The housing can be formed from a semi-rigid silicone or other semi-stiff material. The top portion 14 includes a first nozzle 18 and a second nozzle 20. The first and second nozzles 18 and 20 can take the form of connectors, such as a barbed connector, press-fit connector, frictional connector, twist-and-lock connector, or any other suitable configuration known to one of skill in the art. The bottom portion 16 includes a skirt 22. The skirt 22 can be used to secure the valve assembly 10 to a blood vessel or other tissue of a patient. The skirt can be formed from a Dacron™, ePTFE, or any other flexible and easily suturable material known in the art that would be suitable for suturing the skirt 22 to a vessel or other tissue. The components can be preassembled or can be assembled during implantation.

Figure 2:
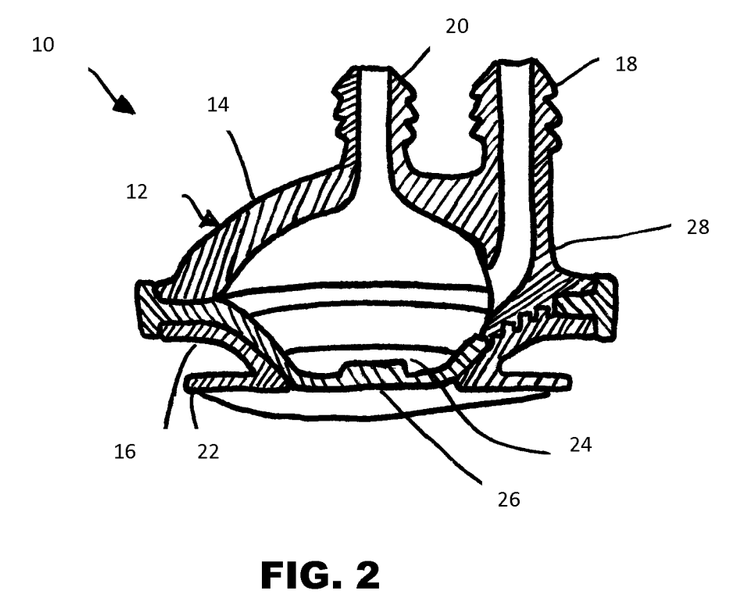
FIG. 2 illustrates a partially sectional view of the valve assembly and a diaphragm disposed within the valve assembly, according to the embodiment of the invention illustrated in FIG. 1.

FIG. 2 illustrates a partially sectional view of a valve assembly 10, according to the embodiment of the invention illustrated in FIG. 1. As illustrated in FIG. 2, the valve assembly 10 includes a housing 12 surrounding a diaphragm 24. The housing 12 can include a two-piece construction having top-portion 14 and bottom portion 16. The housing 12 is illustrated as having a generally spherical shape, but any other suitable shape could be used. The top-portion 14 and the bottom-portion 16 can be coupled together, such that the diaphragm 24 is sandwiched between them. The diaphragm 24 is biased into a closed position, such that the first and second nozzles 18, 20 are open to fluid flow and form a flow path between them. As noted above, with respect to FIG. 1, the housing can be formed from a semi-stiff silicone or other soft and semi-stiff material and the valve can be formed from durable silicone or a silicone-like material with an ePTFE coating at the surface 26 of the valve that is in contact with a flow of blood through the large-diameter vein. It should be noted that any suitable materials or coating that are known to one of ordinary skill in the art could also be used to construct the valve. Any material used should be configured to tolerate sterilization methods such as ethyleneoxide, gamma irradiation, or autoclaving. The components of the valve assembly 10 can be formed in any number of ways known to one of skill in the art, such as molding. Additionally the components of the valve assembly 10 can be joined in any way known to one of skill in the art, such as, but not limited to heat sealing, securing with a fastener, or adhesive.

Figure 11:
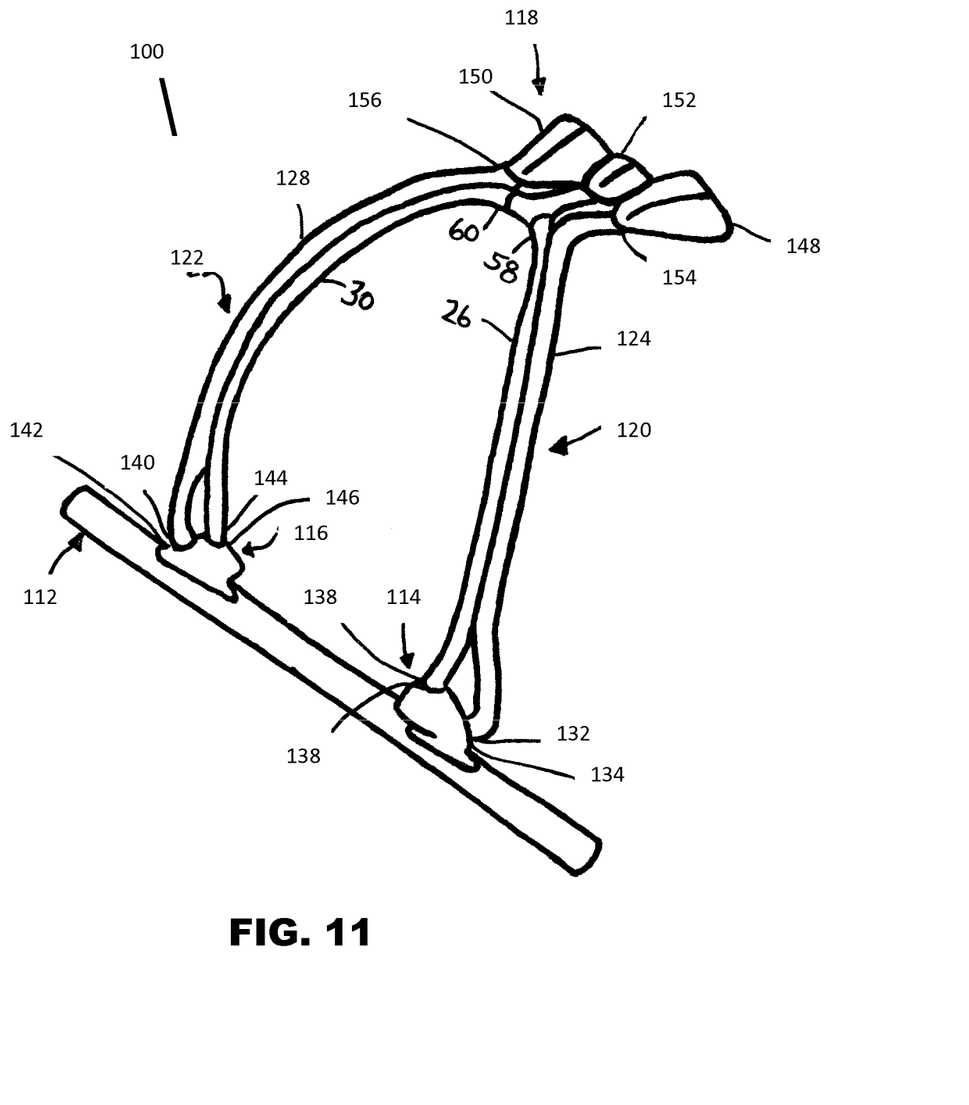
FIG. 11 illustrates a perspective view of a hemodialysis device according to an embodiment of the invention.

As illustrated in FIG. 2, the first nozzle 18 directs the flow of fluid into or out of the valve assembly 10. The second nozzle 20 is incorporated into the housing 12 such that the valve assembly 10 can be opened and closed with fluid pressure and cleaning fluid can be introduced into the system. As illustrated in FIG. 2, the first nozzle 18 can include a fluted flow channel 28, which funnels fluid immediately to reduce the shear stress that the diaphragm 24 is exposed to and in turn increases the stability of the diaphragm 24. The first and second nozzles 18 and 20 can be arranged in parallel as illustrated in FIG. 2 or perpendicularly, as illustrated in FIG. 11, described below.

Further, as illustrated in FIG. 2, the bottom-portion 16 of the housing 12 includes the flap or skirt 22 that can be formed from a Dacron, ePTFE, or any other flexible and easily sutured material known in the art. When implanted for use with hemodialysis, a 1 cm incision is made to the vein and the skirt 22 is sutured to the edges of the incision. The skirt 22 is flexible, but pre-shaped to fit flush with the preferably 7-9 mm vein. When the diaphragm 24 is in the closed position, it is tight against the lower housing, and flush with the anastomosed skirt, allowing for undisturbed blood-flow past the device when off-dialysis.

Figure 3:
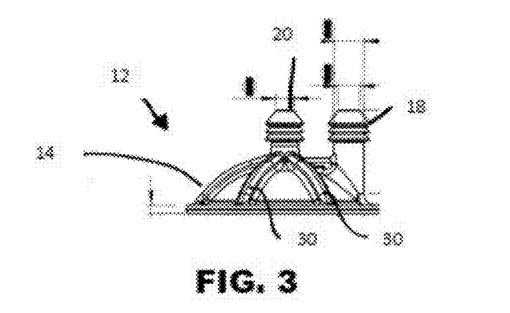
FIG. 3 illustrates a first side view of an outer housing according to an embodiment of the invention.
Figure 4:
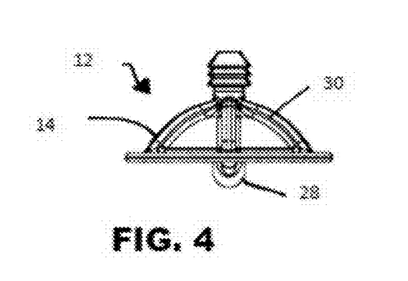
FIG. 4 illustrates a second side view of the outer housing according to the embodiment of the invention illustrated in FIG. 3.
Figure 5:
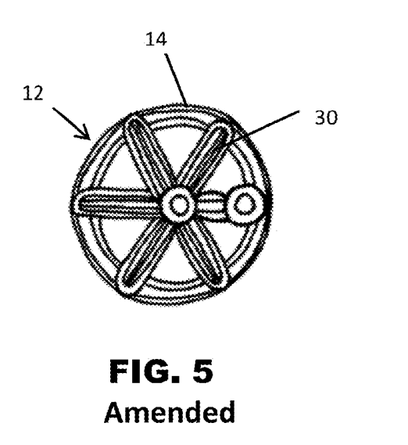
FIG. 5 illustrates a top down view of the outer housing according to the embodiment of the invention illustrated in FIGS. 3 and 4.
Figure 6:
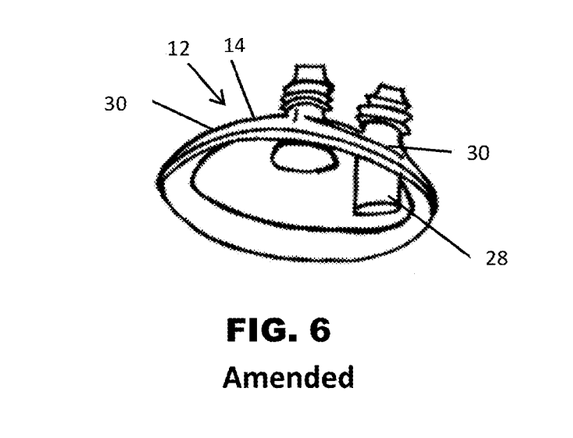
FIG. 6 illustrates a perspective view of an inner housing according to the embodiment of the invention illustrated in FIGS. 3-5.

FIG. 3 illustrates a first side view of an outer housing according to an embodiment of the invention, and FIG. 4 illustrates a second side view of the outer housing according to the embodiment of the invention illustrated in FIG. 3. FIG. 5 illustrates a top down view of the outer housing according to the embodiment of the invention illustrated in FIGS. 3 and 4, and FIG. 6 illustrates a perspective view of an inner housing according to the embodiment of the invention illustrated in FIGS. 3-5. In the embodiment illustrated in FIGS. 3, 4, and 5, the housing 12 includes the top-portion 14 that includes first and second nozzles 18 and 20. The top-portion 14 also preferably includes ridges 30 that enhance the ridgidity of the housing. FIGS. 4 and 6 further illustrate the structure of the flow channel 28, which directs the flow of fluid into and out of the valve assembly 10. The flow channel 28 is preferably fluted in shape to guide the direction of the flow of blood.

Figure 7:
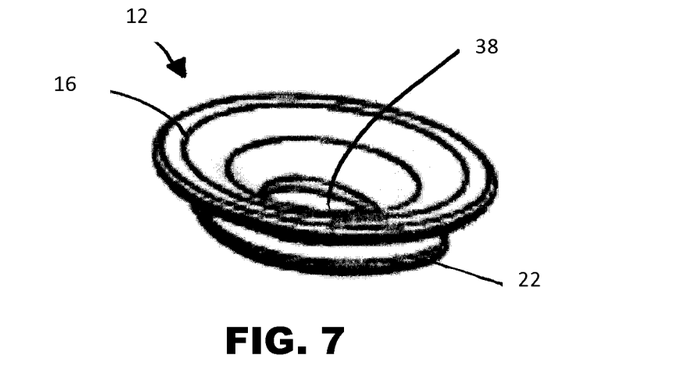
FIG. 7 illustrates a perspective view of a lower housing according to an embodiment of the invention.

FIG. 7 illustrates a perspective view of the bottom portion 16 of the housing 12, according to an embodiment of the invention. The bottom-portion 16 includes the skirt 22 that can be anastomosed to the large-diameter vein, as illustrated in FIG. 11, or attached to any other suitable tissue known to one of skill in the art. When the valve (not shown) is in the open position, fluid can flow through the opening 38 defined by the bottom-portion 16 of the housing 12. The bottom-portion 16 of the housing 12 couples with the top-portion (not shown), in order to sandwich the diaphragm (not shown) in between the two portions of the housing 12. Therefore, both the bottom-portion 16 and the top-portion (not shown) are configured to be coupled, to form a fluid-tight structure surrounding the diaphragm 24.

Figure 8:
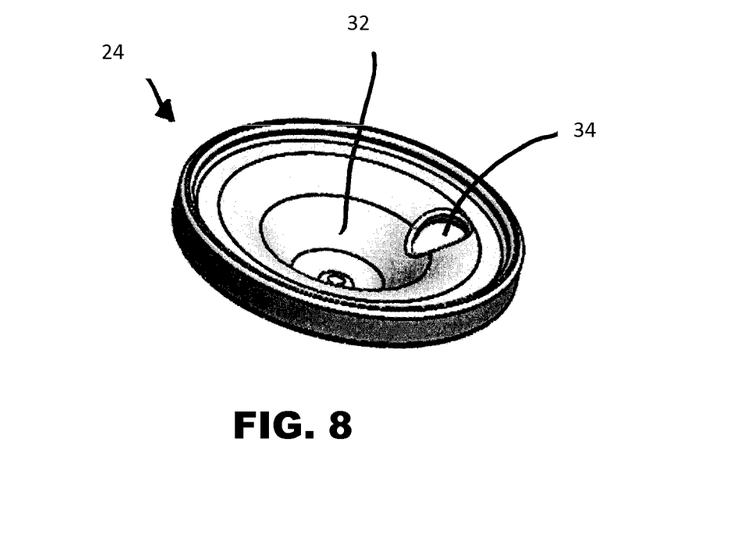
FIG. 8 illustrates a perspective view of a valve according to an embodiment of the invention.

FIG. 8 illustrates a perspective view of a valve according to an embodiment of the invention. As described above, the diaphragm 24 is configured to sit between the top-portion (not shown) of the housing 12 and the bottom-portion (not shown) of the housing 12. The diaphragm 24 is further configured to have hang-down 32 that is flush with the skirt (not shown), when the diaphragm 24 is in the closed position. The diaphragm 24 also defines an opening 34, through which the flow channel (not shown) extends, when the diaphragm 24 is in an open position. This helps to secure the valve in place between the top-portion (not shown) and the bottom-portion (not shown) of the housing (not shown) and also allows for the flow of blood through the valve and out of the valve assembly (not shown) through nozzle (not shown).

Figure 9:
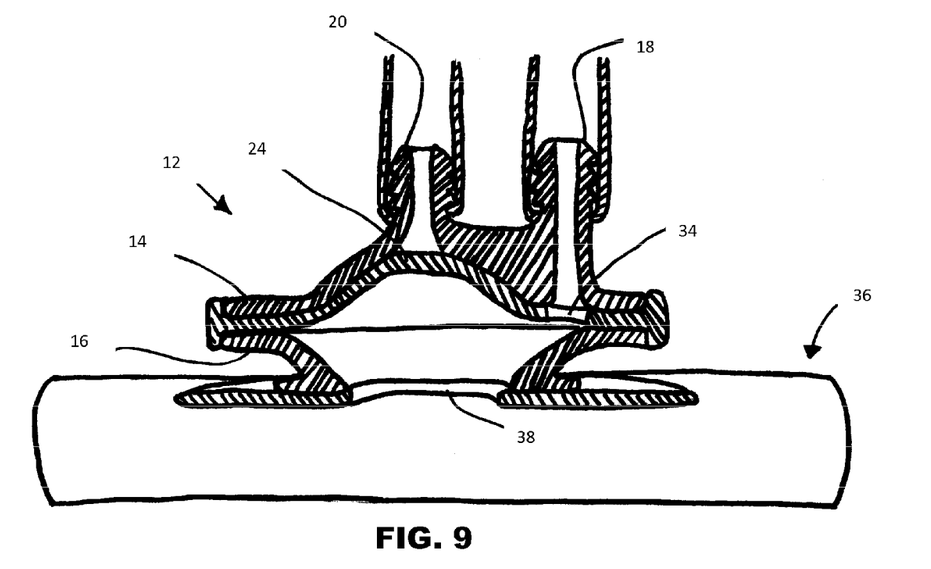
FIG. 9 illustrates a partially sectional view of an open valve according to an embodiment of the invention.
Figure 10:
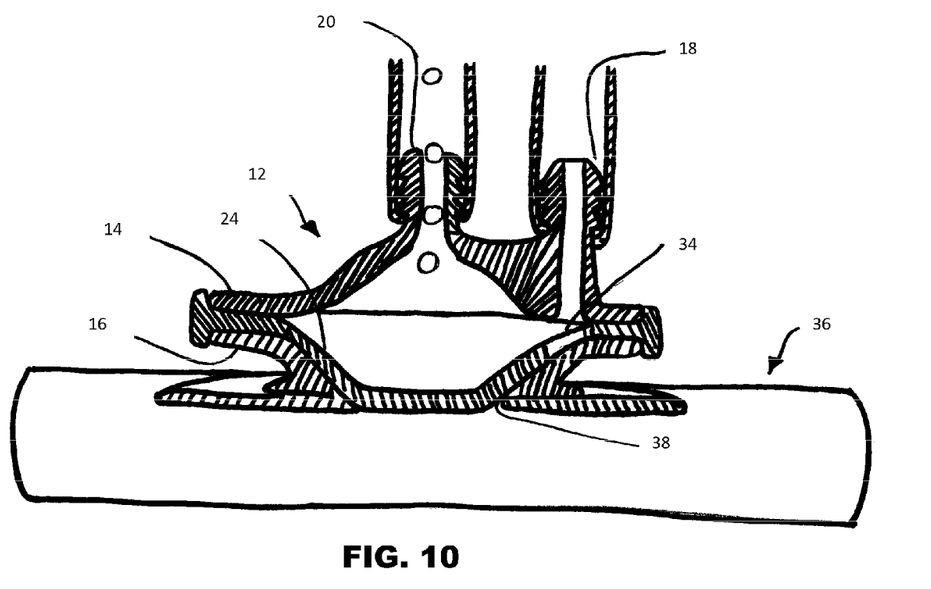
FIG. 10 illustrates a partially sectional view of a closed valve according to an embodiment of the present invention.

FIG. 9 illustrates a sectional view of the valve assembly 10 having an open diaphragm 24, according to an embodiment of the invention and FIG. 10 illustrates a sectional view of the valve assembly 10 having a closed diaphragm 24, according to an embodiment of the present invention. As described above, when negative pressure is applied to the diaphragm 24, the diaphragm 24 is opened, as illustrated in FIG. 9, and when positive pressure is applied to the diaphragm 24, the diaphragm 24 is closed, as illustrated in FIG. 10. The diaphragm 24 is biased to be in the closed position. FIGS. 9 and 10 both show the diaphragm 24 disposed within housing 12 of the valve assembly 10. As described with respect to FIG. 8, the diaphragm 24 defines an opening 34 which, when the diaphragm 24 is open, as in FIG. 9, blood can flow through the opening 34 and through first nozzle 18. In turn, when the diaphragm 24 is closed, as in FIG. 10, the diaphragm 24 is pressed against the bottom portion 16 of the housing 12, such that the opening 34 defined by the bottom portion of the housing is sealed against the flow of liquid between the valve assembly 10 and the large-diameter vein 36.

An exemplary use for the implantable three-way valve described above is as a component of a hemodialysis system. A description of such a hemodialysis system is included herein. However, this exemplary embodiment is not meant to be limiting and the implantable three-way diaphragm valve can be used for any suitable purpose known to one of skill in the art.

FIG. 11 illustrates a perspective view of a hemodialysis device according to an embodiment of the invention. As illustrated in FIG. 11, the hemodialysis device 100 is shown anastomosed to a large-diameter vein 112 such as the femoral vein. The hemodialysis device 100 includes a first valve assembly 114 and a second valve assembly 116 which are both anastomosed to the vein 112. The device 100 also includes a needle-access port 118 that is coupled to the first valve assembly 114 with a first elongate inlet tube 120 and is coupled to the second valve assembly 116, via a second elongate outlet tube 122.

Additionally, as illustrated in FIG. 11, the first elongate inlet tube 120 includes a first lumen 124 and a second lumen 126 and the second elongate outlet tube 122 also includes a first lumen 128 and a second lumen 130. A first end 132 of the first lumen 124 of the first elongate inlet tube 120 couples to a first nozzle 134 on the first valve assembly 114, and a first end 138 of the second lumen 126 couples to a second nozzle 136 on the first valve assembly 114. Similarly, a first end 140 of the first lumen 128 of the second elongate outlet tube 122 couples to a first nozzle 142 on the second valve assembly 116, and a first end 144 of the second lumen 130 couples to a second nozzle 146 on the second valve assembly 116. All of the tubing can be formed from flexible 3-6 mm diameter silicone or silicone-like tubes, with 0.5-1.5 mm wall thickness and include bioengineered collapse prevention. Alternately, the tubing can be formed from any other suitable material known to one of skill in the art.

Figure 12:
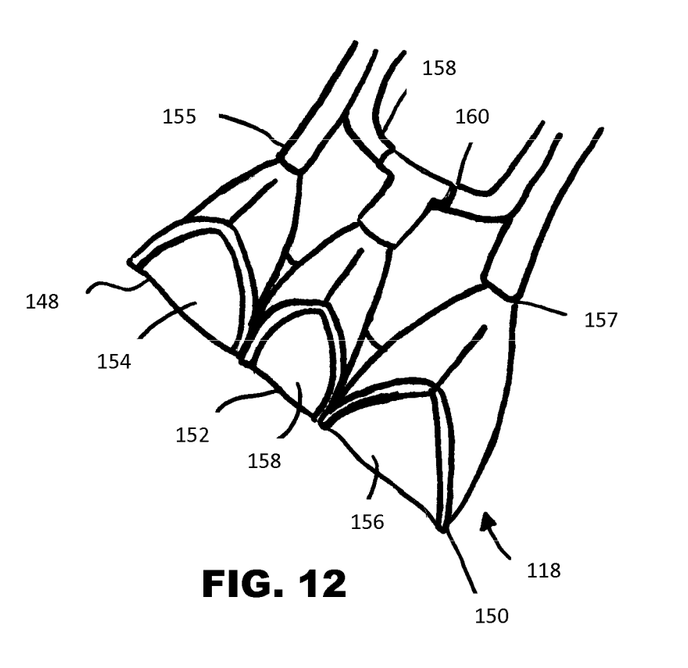
FIG. 12 illustrates a top down view of a triple-port according to an embodiment of the invention.

As illustrated in FIGS. 11 and 12, which illustrates a top down view of a triple-port according to an embodiment of the invention, the needle valve port 118 includes a first septum 148, a second septum 150, and a third septum 152. The first septum 148 couples to a second end 155 of the first lumen 124 of the first elongate inlet tube 120, and the second septum 150 is coupled to a second end 157 of the first lumen 128 of the second elongate outlet tube 122. Therefore, the first septum 148 and the second septum 150 are in fluid communication with a stream of blood traveling through the large-diameter vein 112. In addition, the third septum 152 is coupled to second ends 158, 160 of the second lumens 126, 130 of the first and second elongate inlet and outlet tubes 120, 122. The joined region of second lumens 126 and 130 can also be referred to as a connecting bridge. Therefore, the third septum 152 is in fluid communication with the first and second valve assemblies 114, 116 and, in turn, is in fluid communication with the first lumens 124, 128 of the first and second elongate inlet and outlet tubes 120, 122. The third septum 152 can be used to open and close valve assemblies 114 and 116 using fluid pressure, and can also be used as the hub for injecting and draining a biocompatible cleaning solution from the system.

Further, as illustrated in FIGS. 11 and 12 septa 148 and 150 are larger in size than the third septum 152. The first and second septa 148 and 150 are configured to be tolerant to multiple needle sticks with 14-17 gauge hemodialysis needles. These septa 148 and 150 are large to provide durability for large needle sticks. However, the first and second septa 148 and 150 can also be optimized to have smooth, angled surfaces for patient comfort. The third septum 152 is configured for controlling the valve assemblies 114 and 116. Saline can be pushed into or drained from the third septum 152 through a 22-25 gauge needle. The housing of the needle port 118 can be formed from titanium or a biocompatible polymer and puncture beds 154, 156, and 158 can be formed from a thick silicone or silicone-like layers that seal off around the needle after dialysis is completed. While this embodiment has been described in detail above, it should be known that any configuration known to one of ordinary skill in the art could be used to achieve these results and the above description should not be considered limiting.

Figure 13:
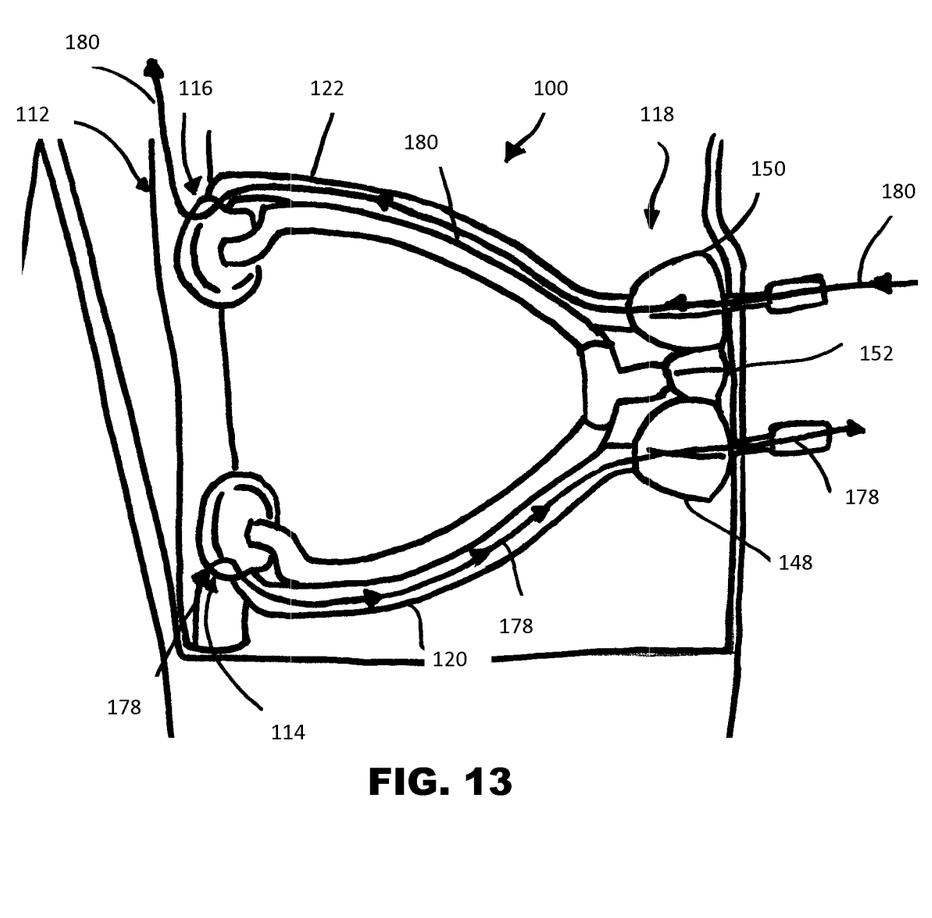
FIG. 13 illustrates a hemodialysis device conducting dialysis according to an embodiment of the present invention.

FIG. 13 illustrates a hemodialysis device conducting dialysis according to an embodiment of the present invention. As illustrated in FIGS. 11 and 13 the valve assemblies 114 and 116 of the hemodialysis device 100 are anastomosed to a large-diameter vein 112. As illustrated by first flow direction arrow 178, shown in FIG. 12, blood flowing through the large-diameter vein 112 travels in through valve assembly 114, through the first lumen 124 of the first elongate inlet tube 120, and out through the first septum 148 of the needle port 118 for hemodialysis processing. After hemodialysis processing is complete, the blood flows back in as illustrated by second flow direction arrow 180. Flow direction arrow 180 follows a path in through the second septum 150 of the needle port 118 through the first lumen 128 of the second elongate outlet tube 122 into valve assembly 116 and back into the large-diameter vein 112.

Figure 14:
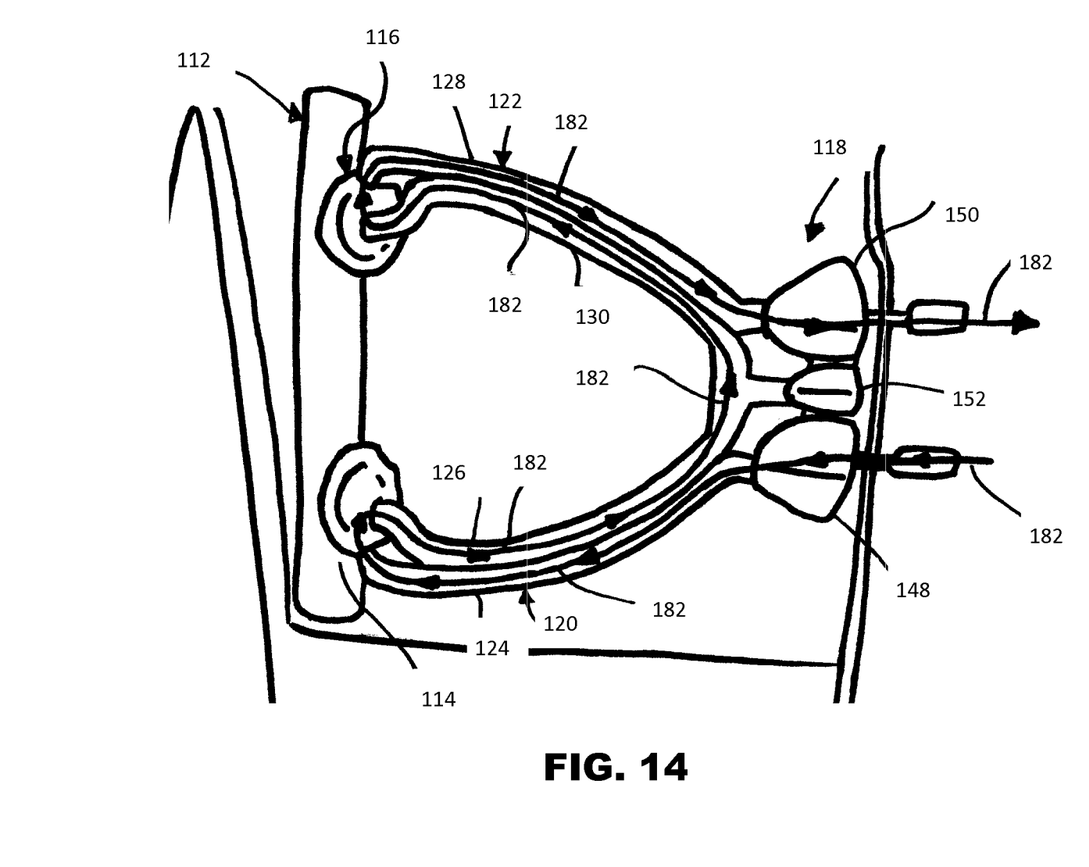
FIG. 14 illustrates a hemodialysis device configured for cleaning according to an embodiment of the present invention.

FIG. 14 illustrates a hemodialysis device configured for cleaning according to an embodiment of the present invention. During cleaning the valve assemblies 114 and 116 are closed to blood flow from the large-diameter vein 112, via the injection of fluid into the third septum 152 of the needle port 118. A cleaning solution can be injected into the device via the first septum 148 of the needle port 118. The cleaning solution follows a cleaning solution flow path 182 in through the first lumen 124 of the first elongate inlet tube 120 into closed valve assembly 114 into the second lumen 126 of the first elongate inlet tube 120 across bridge 184 and into the second lumen 130 of the second elongate outlet tube 122. The path 182 continues through the valve assembly 116 and into the first lumen 128 of the second elongate outlet tube 122 and then out through the second septum 150 of the needle port 118.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A valve comprising:
a housing having a top portion and a bottom portion;
a first nozzle defined by the top portion;
a second nozzle defined by the top portion;
an opening defined by the bottom portion of the housing;
a diaphragm defining a diaphragm opening, the diaphragm having an open position, such that the diaphragm sits in a valve seat defined by the top portion of the housing and such that in the open position the diaphragm opening is aligned with the first nozzle defined by the top portion, and the diaphragm having a closed position, such that the diaphragm sits in a valve seat defined by the bottom portion of the housing and such that the diaphragm opening sits against a wall of the bottom portion of the housing and is occluded to fluid flow, said diaphragm being disposed between the top housing portion and the bottom housing portion, and wherein when the diaphragm is in the closed position the opening defined by the bottom portion of the housing is completely occluded to fluid flow.

2. The valve of claim 1 further comprising a first fluid flow path between the first nozzle and the second nozzle, said first fluid flow path being defined by the housing and the diaphragm, when the diaphragm is in the closed position.

3. The valve of claim 1 further comprising a second fluid flow path between the opening and the first nozzle, said second fluid flow path being defined by the housing and the diaphragm, when the diaphragm is in the open position.

4. The valve of claim 1 further comprising the diaphragm being configured to be movable from the open position to the closed position using positive pressure, and said diaphragm further being movable from the closed position to the open position using negative pressure.

5. The valve of claim 1 wherein the housing and diaphragm are formed from biocompatible materials.

6. The valve of claim 1 wherein the diaphragm is formed from an implantable grade silicone.

7. The valve of claim 1 further comprising the diaphragm being coated with an antithrombogenic material.

8. The valve of claim 1 further comprising the diaphragm being coated with ePTFE.

9. The valve of claim 1 wherein the bottom portion of the housing further comprises a skirt configured to be secured to tissue.

10. The valve of claim 9 wherein the skirt is formed from a material selected from one of the group consisting of Dacron and PTFE.

11. The valve of claim 1 wherein the top portion of the housing has ridges along an outer surface of the top portion of the housing.

12. The valve of claim 1 wherein the valve further comprises a fluted opening to direct the flow of blood.

13. The valve of claim 1 wherein the first nozzle and the second nozzle comprise connectors.

14. The valve of claim 13 wherein the first nozzle and the second nozzle comprise connectors selected from one of a group consisting of barbed, press-fit, friction, twist and lock, luer, and threaded.

* * * * *